(12) United States Patent
Nabors et al.

(10) Patent No.: US 7,164,750 B2
(45) Date of Patent: Jan. 16, 2007

(54) NON-DESTRUCTIVE INSPECTION OF MATERIAL IN CONTAINER

(75) Inventors: James Nabors, Wartburg, TN (US); Brook Nash, Knoxville, TN (US); Todd Schrock, Kingston, TN (US); Dick Wyman, Knoxville, TN (US); Norbert Hartwig, Waldems-Esch (DE); Earl Smith, Seymour, TN (US); Adam Williamson, Seymour, TN (US)

(73) Assignee: Smiths Detection, Inc., Alcoa, TN (US)

( * ) Notice: Subject to any disclaimer, the term of this patent is extended or adjusted under 35 U.S.C. 154(b) by 0 days.

(21) Appl. No.: 10/875,503

(22) Filed: Jun. 25, 2004

(65) Prior Publication Data

US 2005/0105680 A1    May 19, 2005

Related U.S. Application Data

(63) Continuation-in-part of application No. 10/629,868, filed on Jul. 30, 2003, now Pat. No. 6,895,072.

(60) Provisional application No. 60/457,319, filed on Mar. 26, 2003.

(51) Int. Cl.
    *G01N 23/04*    (2006.01)

(52) U.S. Cl. .......................................... 378/57; 378/58
(58) Field of Classification Search .................. 378/57, 378/22, 51, 54, 58, 68–69, 62
See application file for complete search history.

(56) References Cited

U.S. PATENT DOCUMENTS

| | | | | |
|---|---|---|---|---|
| 6,005,912 | A * | 12/1999 | Oleppo | 378/57 |
| 6,428,206 | B1 * | 8/2002 | Watanabe | 378/197 |
| 2002/0071520 | A1 * | 6/2002 | Springer et al. | 378/57 |
| 2006/0056583 | A1 * | 3/2006 | Heuft et al. | 378/57 |

* cited by examiner

*Primary Examiner*—Edward J Glick
*Assistant Examiner*—Hoon Song
(74) *Attorney, Agent, or Firm*—Foley & Lardner LLP (57) ABSTRACT

An apparatus and method for non-destructive inspection of materials housed in containers involves orienting an X-ray beam emitter and detector to direct and detect an X-ray beam at an angle substantially parallel to a sloped surface of the container to be inspected. A first X-ray apparatus is located opposite a second X-ray apparatus, and both the first and second X-ray apparatus are adapted to provide two X-ray beams. This arrangement provides for imaging of the entire area of a sloped portion of the container without any shadow or hidden spots.

15 Claims, 7 Drawing Sheets

GLASS IN GLASS QUAD VIEW - TUBE #1 VIEW #1
GLASS JAR WITH METAL LID

FIG. 1
PRIOR ART
GLASS IN GLASS SINGLE VIEW
GLASS JAR WITH METAL LID

GLASS IN GLASS QUAD VIEW - TUBE #1 VIEW #1
GLASS JAR WITH METAL LID

FIG. 4

GLASS IN GLASS QUAD VIEW - TUBE #1 VIEW #2
GLASS JAR WITH METAL LID

GLASS IN GLASS QUAD VIEW - COMBINATION VIEWS
GLASS JAR WITH METAL LID

NON-DESTRUCTIVE INSPECTION OF MATERIAL IN CONTAINER

CROSS-REFERENCE TO RELATED PATENT APPLICATIONS

This application is a continuation-in-part of U.S. patent application Ser. No. 10/629,868, which was filed on Jul. 30, 2003 now U.S. Pat. No. 6,895,072, and is accordingly entitled to the benefit of and priority to U.S. Provisional Application 60/457,319. Both of the aforementioned applications are incorporated by reference herein.

BACKGROUND OF THE INVENTION

This invention concerns the non-destructive inspection of materials housed in containers, and more specifically the inspection of such materials using X-ray beams.

Inspection of various production products has become increasingly important in recent years. Traditionally, product inspection has been limited to physical inspection of the product by a worker on the production line. Obviously, this form of inspection is less than optimal. As such, two more useful devices were developed and became the standard inspection apparatus: a check weigher and a metal detector. Each of these devices has its own inherent limitations, and even the system in combination lacked the ability to provide much information. Therefore, a need exists for an inspection system that can provide more detailed and variable data. The types and breadth of inspection data needed vary from product to product.

It is well-known to carry out non-destructive inspections of materials, including materials in containers, with X-ray beams. In general, a typical basic x-ray device is a linear array comprising a high voltage power supply to power a x-ray tube wherein a beam of x-rays is directed at the product. The x-ray beam passes through the product to ultimately impinge upon a sensor or sensors, such as a row of detector diodes. Such x-rays devices typically then display an image of the material based on the x-rays. This image can provide valuable information which a normal optical image cannot. The formation of images due to light or X-ray differs. The major difference is that optical images are created by light reflection on the object surface and X-ray images are formed due to X-rays absorption by passing through a material. Thus, an optical image gives information about the object's surface and an X-ray image supplies information about the inner structure of the object.

An X-ray image is a silhouette, where the degree of transparency is dependent on the density, thickness and the atomic number of the material. Using the current technology this information can be separated and coded into a false color. The atomic number information is coded into the hue value of a color image in HIS (Hue, Intensity, Saturation) format. The mixed information about the thickness and the density is coded into intensity of a color. A certain percentage of X-ray energy is absorbed by the material due to a process known as electron ionization. The amount of energy absorbed depends on the density and atomic number of the material. As a result, the detected X-ray attenuation provides a picture of the absorbed energy on the irradiated objects. Due to the absorbed energy being relative to the atomic number, it can be used in the material discrimination process.

In general, the lower the atomic number, the more transparent the material is to the X-rays. Materials composed of elements with a high atomic numbers absorb radiation more effectively causing darker shadows in an X-ray image. Substances with low atomic numbers absorb less X-ray radiation, hence their shadowgraph appears a lighter color. The absorption of the X-ray radiation by a material is proportional to the degree of X-ray attenuation and is dependent on the energy of the X-ray radiation and the following material parameters: thickness, density, and atomic number A problem encountered when using such apparatus and systems, especially when inspecting food in containers, is that the geometry of the containers often causes undue lines in detector images thereof, which detract from the quality of such images and, therefore, negatively affect interpretations of the images. None of the apparatus and methods described in the above-mentioned patents adequately overcomes this problem. X-ray inspection of food products in glass jars to eliminate broken glass contaminants presents a unique challenge due to the crown typically found in the jar bottom. Single view systems are offered but the coverage on the jar bottom is limited as this crown will "hide" the contaminant resulting in the fact that the contaminant must be of a size large enough to extend above the crown as viewed by the x-ray system. These systems are designed with a geometry of shooting the x-ray beam parallel to the jar bottom. If the jar bottom were perfectly flat then 100% coverage of the jar bottom can be achieved. The amount of the crown ajar exhibits determines how much of the jar bottom a single view system can effectively inspect. The larger the crown, the less coverage of the jar bottom is achieved. Typical crowns range between about 4.0 mm and about 12.0 mm in height. A single view system well effectively cover, for example, about 40% of the jar bottom for a 4.0 mm crown height. This coverage is reduced as the crown becomes larger, for example, to about 20% for a crown of 12.0 mm.

Dual view x-ray systems are known where the x-ray beams are at a 90° angle from one and other, both beams being parallel to the jar bottom. This increases the coverage of the jar bottom to between 40% and 80% depending on the crown height. A number of the systems described in these patents employ two or more X-ray beams at substantial angles to one another for producing two or more images that can be interpreted from the two different perspectives. This increases an amount of information available for interpreting the images.

Thus, it is an object to provide an X-ray inspection apparatus (as well as a method) that produces an intuitive, easy-to-read detector image of material in conveyed containers.

SUMMARY OF THE INVENTION

According to an embodiment, an apparatus and method for non-destructive inspection of materials housed in containers are provided. The method includes orienting an X-ray beam emitter and detector to direct and detect a first X-ray apparatus on a first side of a conveyor along which the materials are conveyed. A second X-ray apparatus is located on the opposite side of the conveyor. Each X-ray apparatus is adapted to provide at least two X-ray beams, such as through the use of a dual beam generator, with each X-ray beam having a corresponding X-ray detector. For example, the X-ray apparatus may be adapted to have four X-ray detectors. In a preferred embodiment, by using two x-ray apparatus located on opposite sides of a conveying line, each having two detector apparatus in association therewith, the present invention is able to provide an improved image of the bottom crown of a container. Preferably, the two X-ray beams on each side of the conveyor are angled 45° with respect to each other (22.5° with respect to the conveyor).

It is to be understood that both the foregoing general description and the following detailed description are exemplary and explanatory only, and are not restrictive of the invention as claimed.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

The invention is described and explained in more detail below using the embodiments shown in the drawings. The described and drawn features, in other embodiments of the invention, can be used individually or in preferred combinations. The foregoing and other objects, features and advantages will be apparent from the following more particular description of preferred embodiments of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION

Figure 2:
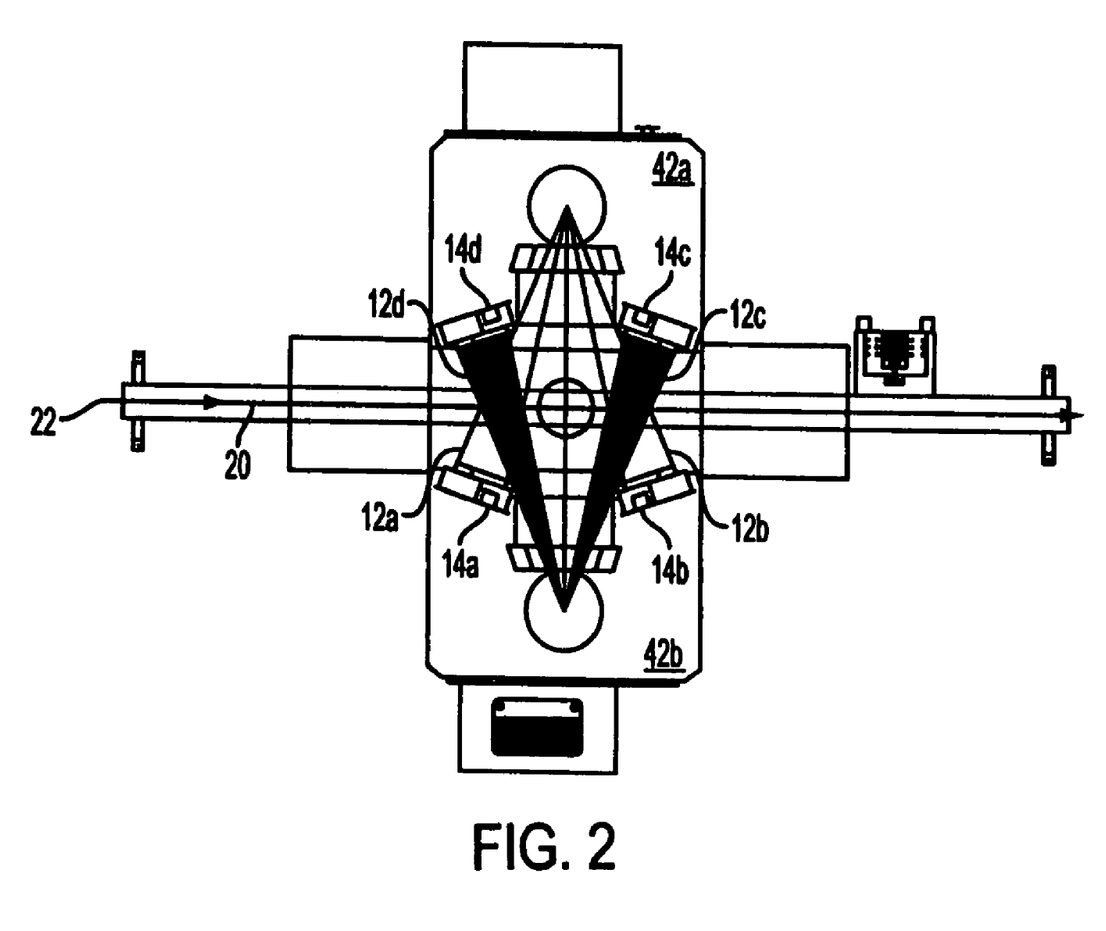
FIG. 2 is a top-view of an apparatus of the present invention having two dual beam x-ray generators on opposite sides of a path of the object to be scanned and each in communication with two detectors opposite their respective x-ray generators.

The present invention provides a system and method which eliminate the "hidden" areas of the prior art systems by orienting the x-ray beams to be parallel to the slope of a crown 10 in the container 16. In one embodiment illustrated in FIG. 2, system has a structure of two x-ray apparatus 42a and 42b oriented on opposite sides of the conveyor 20 traveling through the system. Each apparatus emits a dual beam at 45° from one and other. Four x-ray sensor devices 14a, 14b, 14c, 14d are placed on the opposite side of the conveyor from their respective tube. This inspection structure with two dual beam tubes and four sensors allows substantially 100% inspection of the glass jar bottom.

Figure 1:
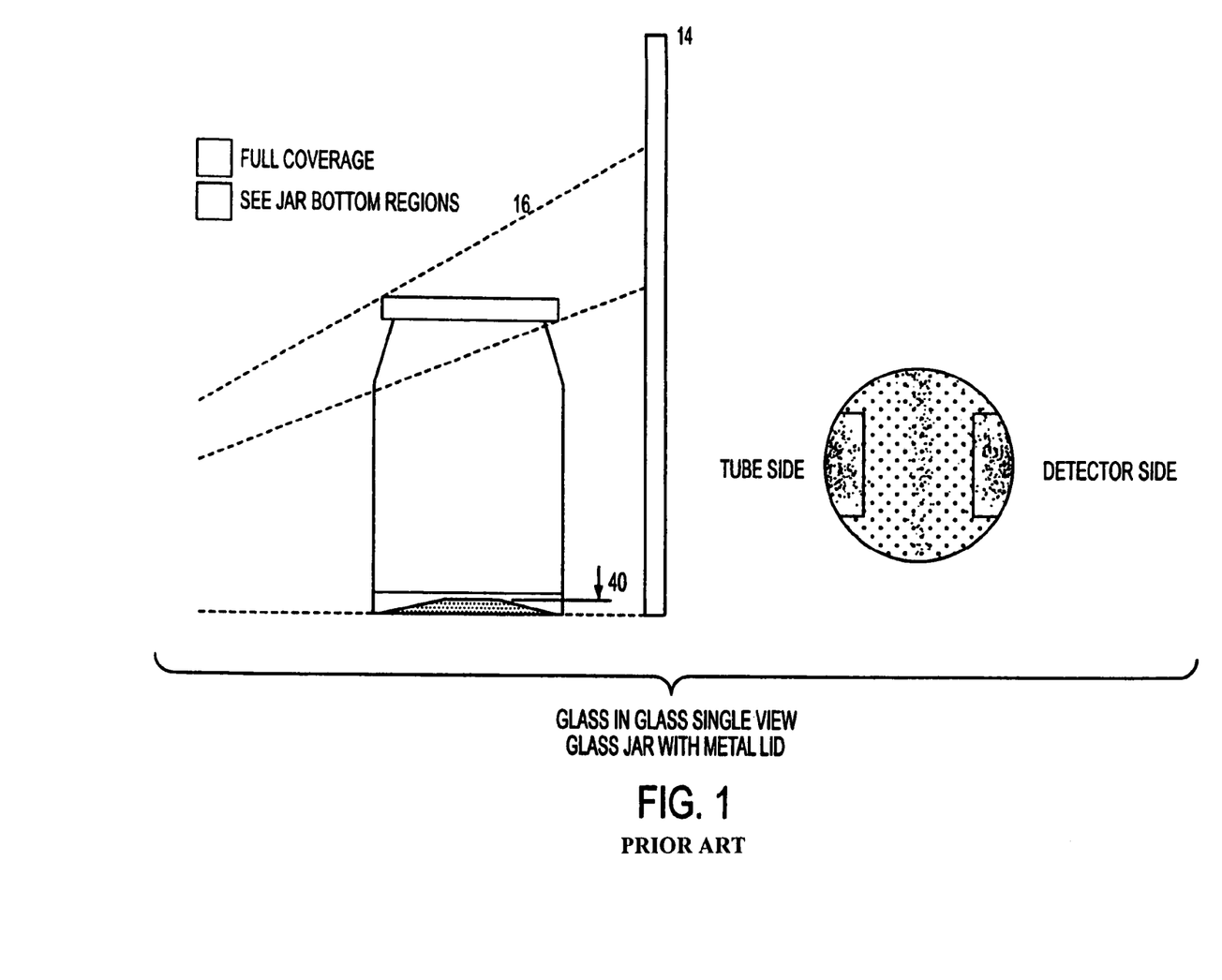
FIG. 1 is a view of a prior art apparatus wherein a single view is used.

FIG. 1 depicts the area of a crown 40 detected by an apparatus of the prior art. The prior art apparatus does not provide adequate detection as it is capable of detecting only a small portion of the area below the crown 40, and the angle of crown creates difficulty in obtaining a clean image of even that area.

Figure 3:
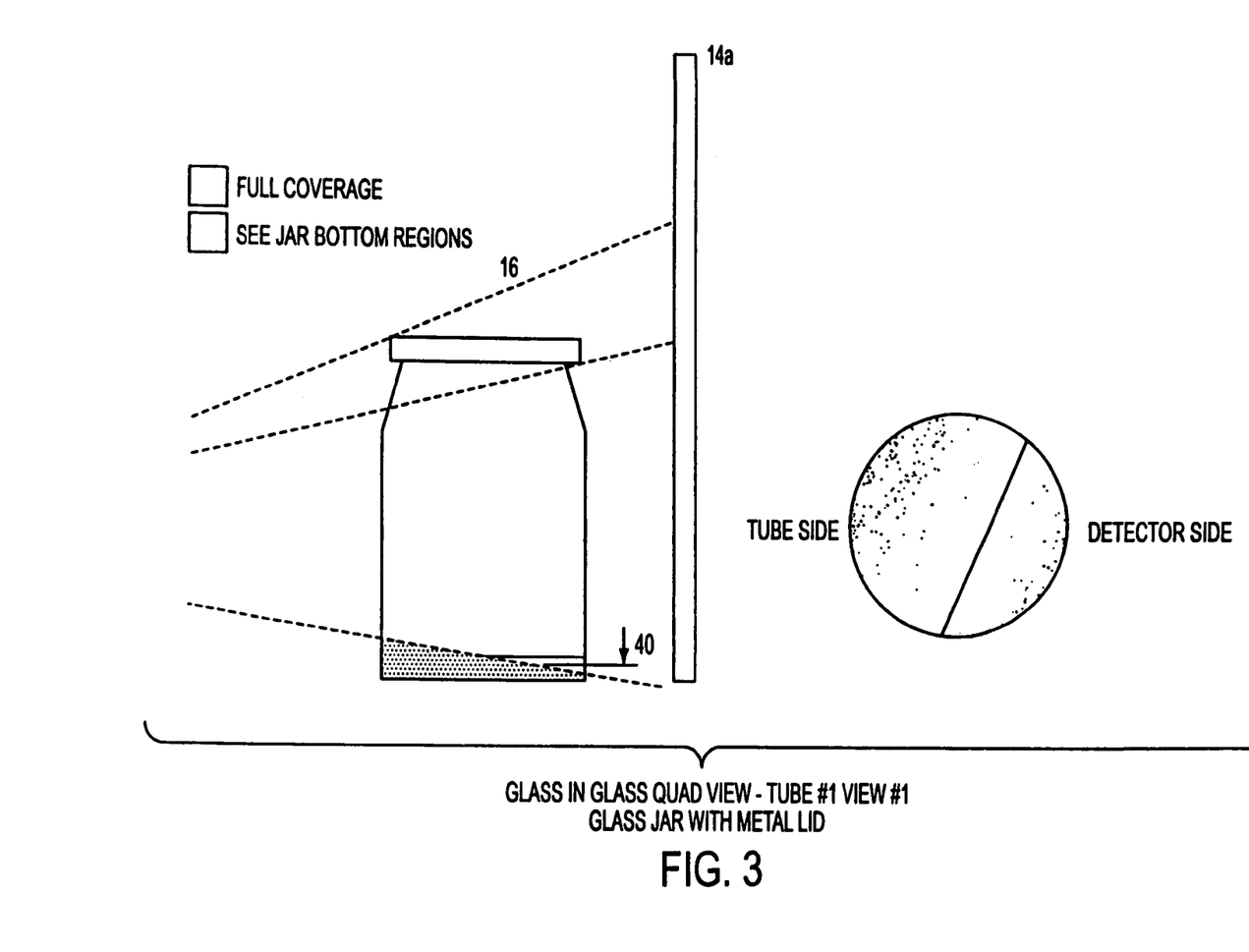
FIG. 3 is a view of an apparatus in accordance with the principles of the present invention depicting a first view from a first x-ray apparatus.

FIG. 3 depicts a first view of a four view (i.e. four beams and detectors) system. This view provides a full coverage of 40% of the jar bottom that is on the detector side of the conveyor. The second view shown in FIG. 4 also covers 40% of the jar bottom but is at a 45° angle from the first view and thus shifts the full coverage by 45°. The combination of these two views results in full coverage of 60% of the jar bottom with an overlap between the two views.

Figure 4:
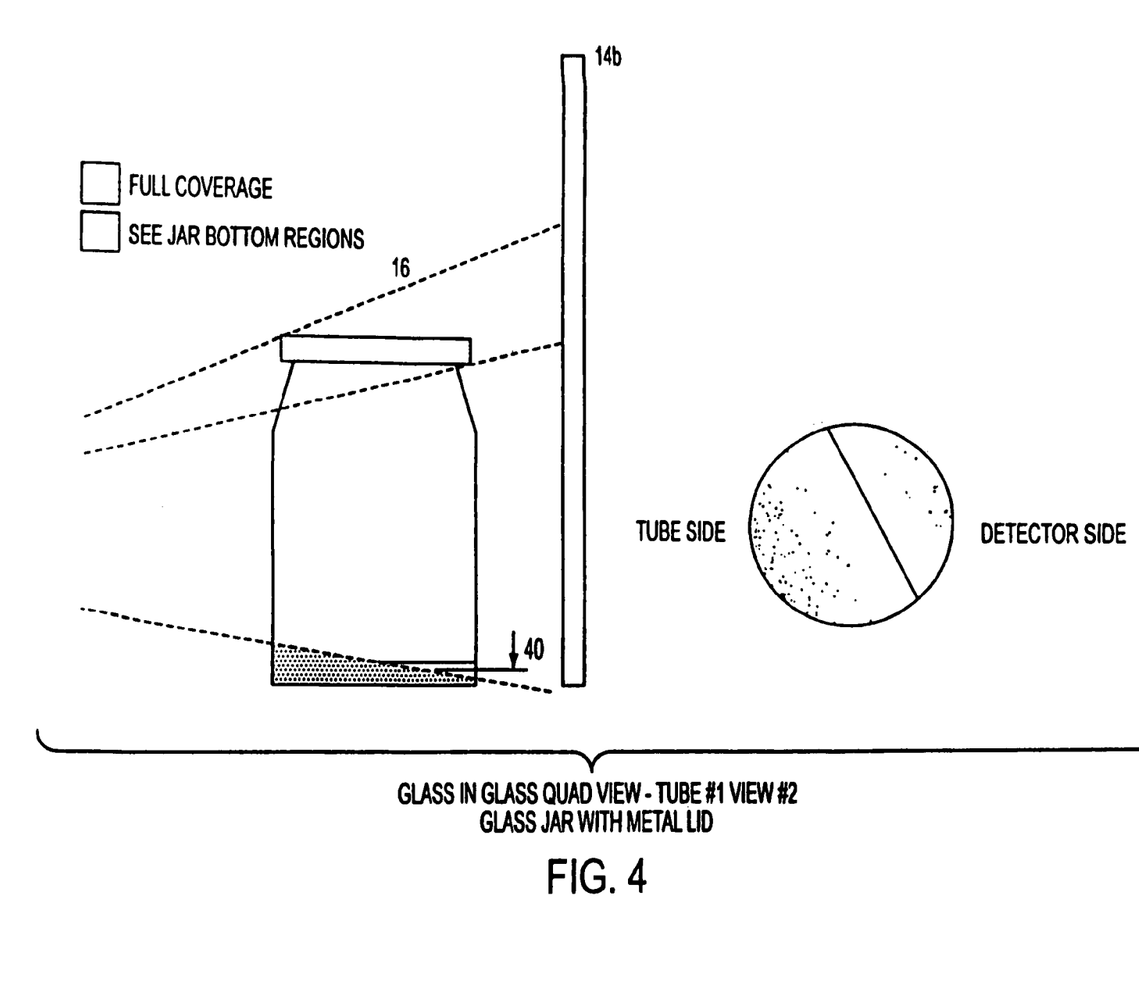
FIG. 4 is a view of an apparatus in accordance with the principles of the present invention depicting a second view from a first x-ray apparatus.
Figure 5:
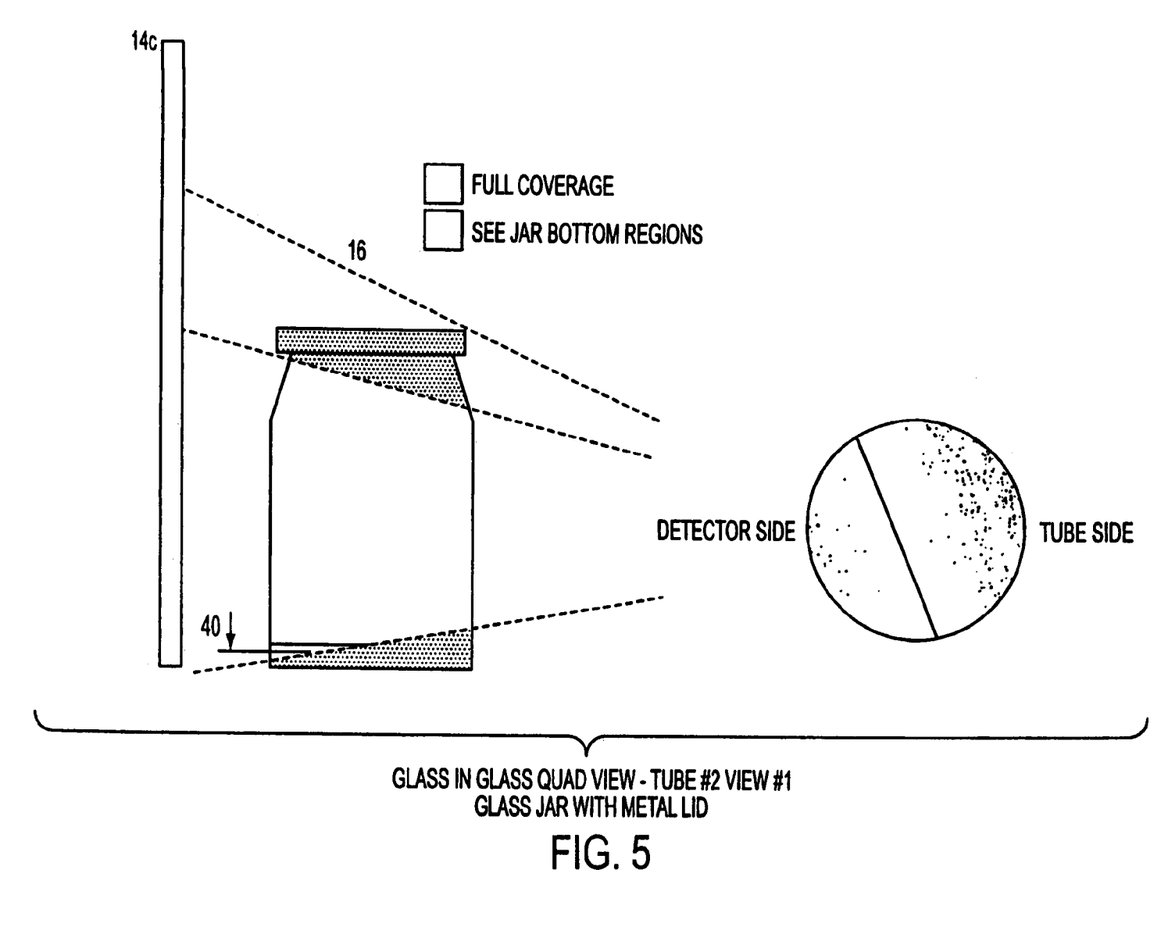
FIG. 5 is a view of an apparatus in accordance with the principles of the present invention depicting a first view from a second x-ray apparatus.
Figure 6:
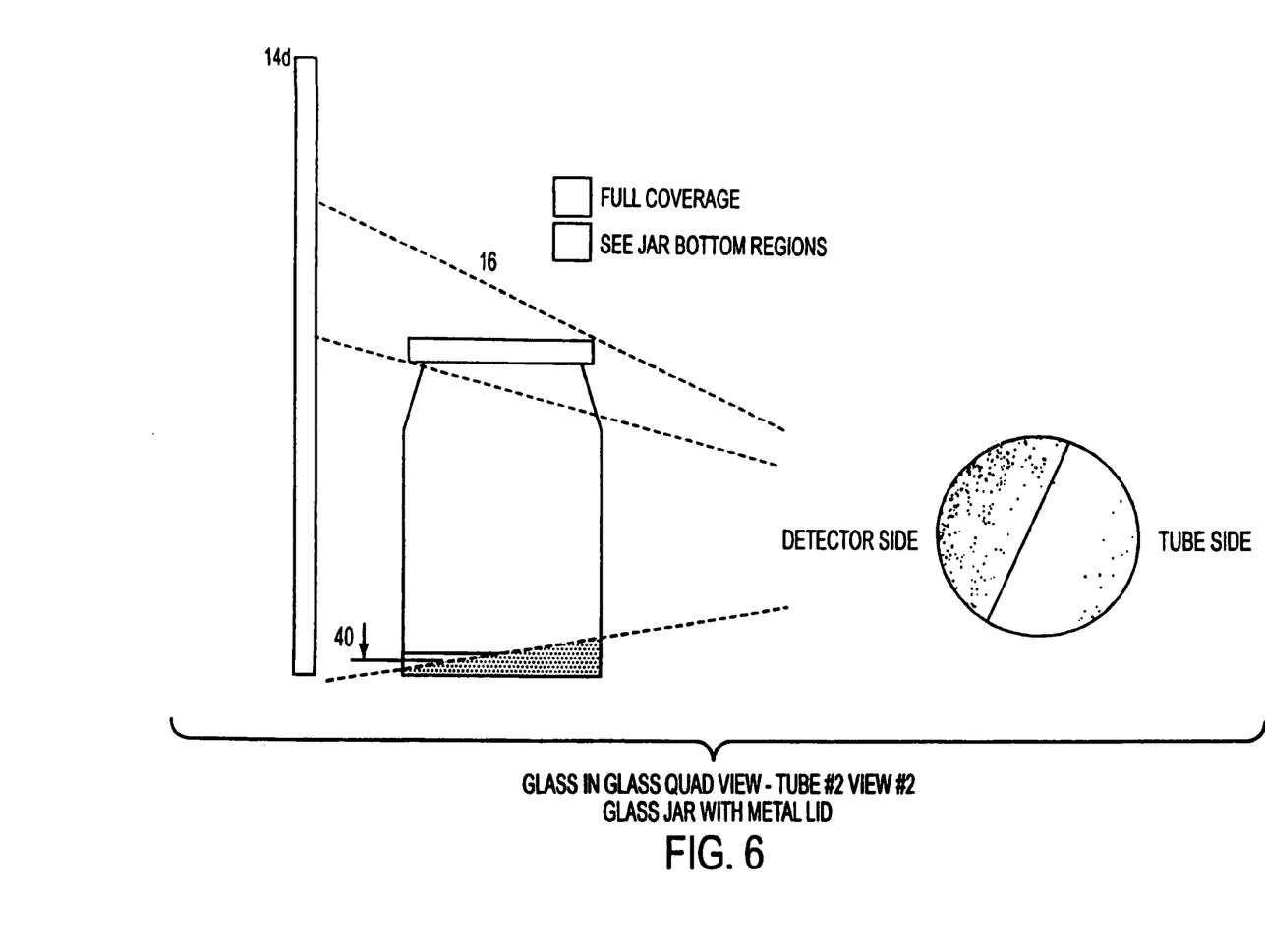
FIG. 6 is a view of an apparatus in accordance with the principles of the present invention depicting a second view from a second x-ray apparatus.

The third view shown in FIG. 5 represents the results of a detector on the opposite side of the conveying line in regard to the detectors shown in FIGS. 3 and 4. This view provides full coverage of 40% of the jar bottom, opposite the first view by changing the tube/detector relationship such that the x-ray beam is shot from the opposite side of the jar. The result is picking up an additional 20% of the jar bottom for full coverage and adding to the overlap. The fourth view shown in FIG. 6 adds the final 20% of the jar bottom for full coverage.

Figure 7:
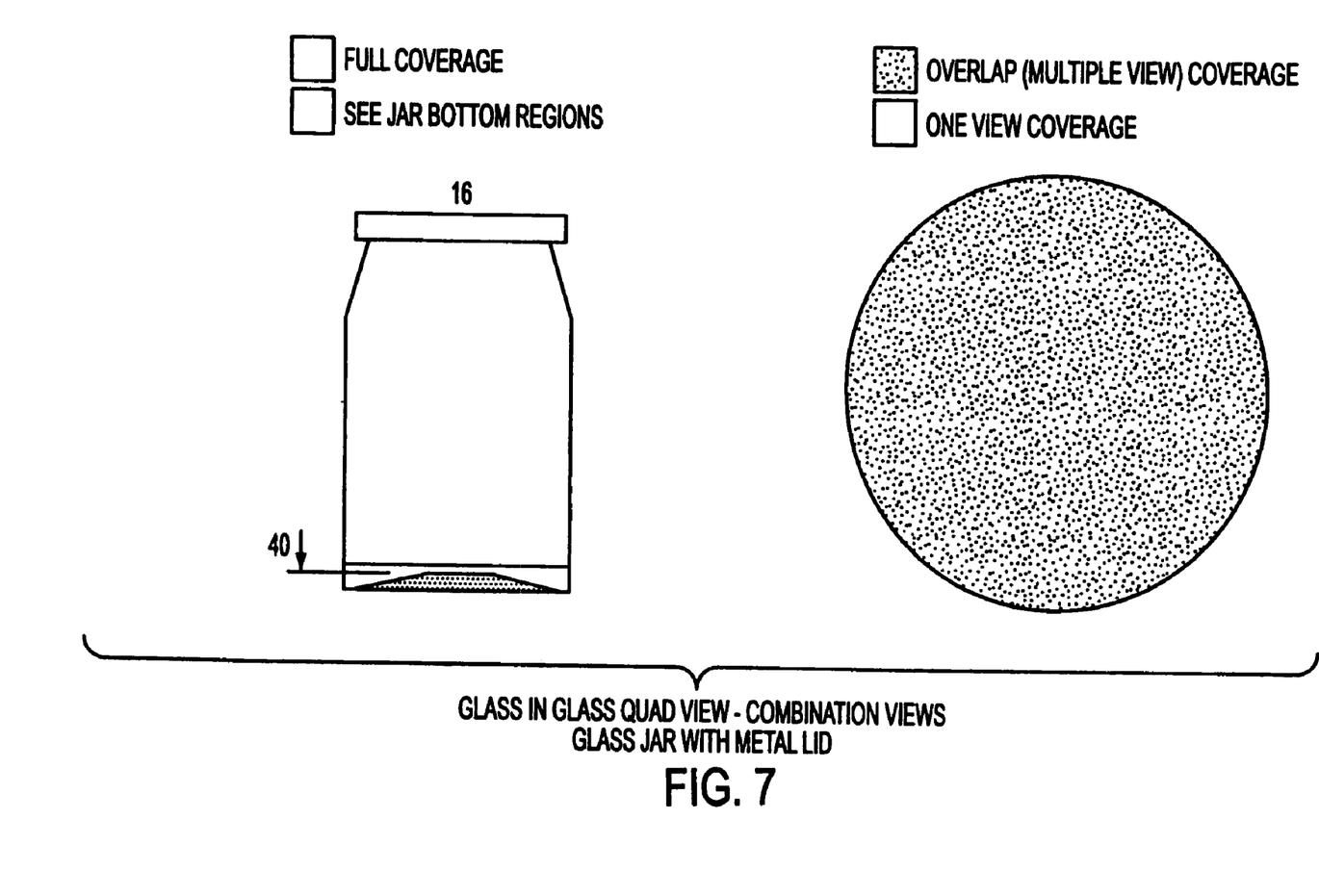
FIG. 7 is a view of an apparatus in accordance with the principles of the present invention depicting the composite of the views shown in FIGS. 3–6.

Combining the four views, as shown in FIG. 7, allows for each individual view to be optimized for the 40% of the jar bottom that the view is inspecting and ignoring the 60% of the jar bottom because the addition views will cover that area. Thus an improved image of substantially 100% of the jar bottom is obtained with no shadows or hidden areas.

While the invention has been particularly shown and described with reference to a preferred embodiment, it will be understood by those skilled in the art that various changes in form and detail may be made therein without departing from the spirit and scope of the invention.

In addition, an apparatus and method in accordance with the principles of the present invention may further comprise various additional inspection features such as but not limited to check-weighing capability, missing item detector, void detection, and reject stations. The reject station may utilize, but is not limited to, a signal only, an indicator light, a single lane air blast, a single piston side push arm, a vertical side impulse push arm, or a horizontal side impulse push arm.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. An apparatus for non-destructively inspecting materials housed in a container having a crown with an inwardly sloping surface on a bottom wall thereof, said apparatus comprising:

a conveyor for conveying said container along a conveying path in a conveying direction;

an first X-ray apparatus having a first X-ray beam emitter mounted at a first position adjacent said conveying path for emitting at least two X-ray beams passing through said container as said container is conveyed along said conveying path;

a second X-ray apparatus having a second X-ray beam emitter mounted at a second position adjacent said conveying path for emitting at least two X-ray beams, wherein the second X-ray beam emitter is substantially opposite the first X-ray beam emitter;

at least two detectors mounted adjacent said conveying path on a side of said conveying path opposite that of said first X-ray beam emitter for receiving a portion of the X-ray beams that has passed through said container and generating therefrom at least two image signals representative of the portion;

at least two detectors mounted adjacent said conveying path on a side of said conveying path opposite that of said second X-ray beam emitter for receiving a portion of the X-ray beams that has passed through said container and generating therefrom at least two image signals representative of the portion;

wherein said first and second X-ray beam emitters are positioned to direct a portion of the X-ray beams along a path that substantially parallels the sloping surface of the crown.

2. The apparatus of claim 1, wherein the first X-ray apparatus and the second X-ray apparatus are adapted to each provide two X-ray beams to two detectors.

3. The apparatus of claim 1, wherein the first X-ray beam emitter emits a first X-ray beam and a second X-ray beam, wherein the angle formed by the first X-ray beam and the second X-ray beam is about 45°, and wherein the second X-ray beam emitter emits a third X-ray beam and a fourth X-ray beam, wherein the angle formed by the third X-ray beam and the fourth X-ray beam is about 45°.

4. The apparatus as in claim 1, wherein the path is at the sloping surface.

5. The apparatus as in claim 1, wherein the path is immediately proximate to the sloping surface.

6. The apparatus as in claim 1, wherein that apparatus detects substantially 100% of the container bottom.

7. A method for non-destructive inspection of material housed in a container having an inwardly protruding crown on a bottom wall thereof, said method comprising:

conveying the container along a conveying path;

passing at least four X-ray beams through said container as said container is conveyed along said conveying path;

receiving a portion of the at least four X-ray beams passed through said container; and generating a signal representative of the portion of the at least four X-ray beams and therefore of an image representative of said material;

wherein a portion of said at least four X-ray beams is directed along a path that substantially parallels a sloping surface of the inwardly protruding crown.

8. The method of claim 7, further comprising the step of aligning a first X-ray beam and a second X-ray beams substantially at a 45° angle with respect to each others and further comprising aligning a third X-ray beam and a fourth X-ray beam substantially at a 45° angle with respect to each other.

9. The method as in claim 7, wherein substantially 100% of the container bottom is detected.

10. An apparatus for non-destructively inspecting materials housed in a container having a inwardly protruding crown on a bottom wall thereof and adapted to travel along a conveying path, said apparatus comprising:

a first x-ray apparatus having a first X-ray beam emitter mounted at a first X-ray position adjacent the conveying path, wherein the first X-ray beam emitter emits at least two X-ray beams;

a first detector and a second detector mounted adjacent said conveying path on a side of said conveying path opposite that of said first x-ray apparatus for receiving a portion of the at least two X-ray beams that has passed through the container;

a second X-ray apparatus having a second X-ray beam emitter mounted at a second X-ray position adjacent the conveying path and substantially opposite the first X-ray apparatus, wherein the second X-ray emitter emits at least two X-ray beams; and a third detector and a fourth detector mounted adjacent said conveying path on a side of said conveying path opposite that of said second X-ray apparatus for receiving a portion of the at least two X-ray beams that has passed through the container;

wherein the first and second X-ray apparatus are positioned to direct a portion of the X-ray beams at an angle along a path that substantially parallels the slope of the crown.

11. The apparatus of claim 10, wherein the first X-ray apparatus comprises a dual beam generator.

12. The apparatus of claim 10, wherein the second X-ray apparatus comprises a dual beam generator.

13. The apparatus of claim 10, wherein the first X-ray apparatus emits a first X-ray beam and a second X-ray beam, and wherein the angle formed by the first X-ray beam and the second X-ray beam is about 45°.

14. The apparatus of claim 10, wherein the second X-ray apparatus emits a first X-ray beam and a second X-ray beam, and wherein the angle formed by the first X-ray beam and the second X-ray beam is about 45°.

15. The apparatus as in claim 10, wherein that apparatus detects substantially 100% of the container bottom.

* * * * *